(12) United States Patent
Clough

(10) Patent No.: US 6,170,176 B1
(45) Date of Patent: Jan. 9, 2001

(54) SHOE APPARATUS AND METHOD

(76) Inventor: James G. Clough, 926 13$^{th}$Ave. South, Great Falls, MT (US) 59405

( * ) Notice: Under 35 U.S.C. 154(b), the term of this patent shall be extended for 0 days.

(21) Appl. No.: 09/467,973

(22) Filed: Dec. 21, 1999

(51) Int. Cl.$^7$ .................................................. A61F 5/14
(52) U.S. Cl. ..................................... 36/140; 36/71; 36/81; 36/88; 36/117.5
(58) Field of Search .............................. 36/140, 142, 143, 36/144, 159, 155, 172, 71, 81, 117.5, 28, 88

(56) References Cited

U.S. PATENT DOCUMENTS

| | | | |
|---|---|---|---|
| 1,847,973 | * | 8/1932 | Morton .................................... 36/180 |
| 3,964,181 | * | 6/1976 | Holcombe, Jr. ..................... 36/2.5 R |
| 4,914,837 | * | 4/1990 | Rieffel ........................................ 36/88 |
| 4,934,073 | * | 6/1990 | Robinson ................................. 36/91 |
| 5,345,701 | * | 9/1994 | Smith ....................................... 36/144 |
| 5,491,912 | * | 2/1996 | Snabb et al. .......................... 36/114 |
| 6,041,523 | * | 3/2000 | Deloreia ................................... 36/71 |
| 6,098,319 | * | 8/2000 | Epstein .................................. 36/159 |

* cited by examiner

*Primary Examiner*—Paul T. Sewell
*Assistant Examiner*—Jila Mohandesi

(57) ABSTRACT

An orthopedic shoe appliance is provided having a pad with a wedge. The wedge is located on the pad in the area where the big toe would rest on the pad. The wedge provides a means to elevate the big toe up from the top planar surface of the pad. The relation between the pad and the wedge is defined by an angle. The angle is preferably in the range of from 20 to 30 degrees for normal ambulation. A method of providing for improved stability of the foot structure during ambulation comprising the steps of providing an orthopedic shoe appliance having a pad, said pad being provided with a wedge, said wedge being located on said pad in an area where a big toe would rest on said pad, said wedge providing a means to elevate said big toe up from a top planar surface of said pad during ambulation, and, said wedge providing an angle.

19 Claims, 1 Drawing Sheet

SHOE APPARATUS AND METHOD

BACKGROUND OF THE INVENTION

The present invention relates to orthopedic shoe appliances specifically adapted to provide improved stability of the foot structure, and a method of providing for improved stability of the foot structure, during ambulation.

When a person ambulates, or moves from place to place such as by walking, a host of triplane motions occur to the foot structure, broadly termed pronation and supination. Pronation generally involves rotation of a joint or part in a forward direction or toward the midline of the body. Supination generally involves rotation of a joint or part in an outward direction or away from the midline of the body. When a person over-pronates, or for any other reason places too much force on the inside of the foot, excessive mobility of the medial arch area of the foot can result. The resulting foot instability can be manifested as arch, foot, ankle, and/or leg pain, as well as postural problems from excessive internal rotation of the leg.

Conventional orthopedic corrective devices described to address this problem include many different types. However, none provide for an orthopedic shoe appliance specifically adapted to provide improved stability of the foot structure, and a method of providing for improved stability of the foot structure, during ambulation in the manner which is provided for in the present invention. The present invention relates more specifically to an orthopedic corrective device that is to be disposed in the footware and applied for the correction and/or treatment of ambulatory mechanical disorders and ensuing physical symptoms.

U.S. Pat. No. 5,881,478, issued Mar. 16, 1999 to McMahon et al. teaches a shoe having a resilient sole, an upper secured to the sole, and a rockable member within a cavity in the sole. The rockable member being configured for side-to-side rocking in the sole cavity between a neutral position and a tilted position as the wearer's foot is moved relative to the sole between a neutral position and a tilted position.

U.S. Pat. No. 5,694,705, issued Dec. 9, 1997 to Alonso Coves teaches an insole formed by the combination of two laminar bodies, one of split leather and the other of rubber material being provided with knobs forming support projections for the foot.

U.S. Pat. No. 4,852,553, issued Aug. 1, 1989 to Voykin teaches a foot zone reflex self-administering therapy apparatus comprising a display board adapted to display foot reflexology zones corresponding to anatomical areas of the body and stimulating members adapted to be placed on the display board at a zone corresponding to an anatomical area of the body requiring therapy.

U.S. Pat. No. 4,414,964, issued Nov. 15, 1983 to Farino et al. teaches a post-operative pliable protector device for the hallux or big toe having a cushion pad with at least a portion thereof adapted to encircle the toe and being formed with a separable fastener having a loop-type fabric.

U.S. Pat. No. 4,408,402, issued Oct. 11, 1983 to Looney teaches a supportive shoe or insert which provides increased support to specific areas of the foot during the first and second trimesters and third trimester of pregnancy to compensate for changes in body weight and center of gravity. A pad, which can be a shoe insole, is provided with these specific areas of support.

U.S. Pat. No. 4,333,472, issued Jun. 8, 1982 to Tager teaches compensatory-corrective orthopedic foot devices comprising of the construction and specific application of a series of differentially-sized geometrically-shaped and specifically configured, generally wedge-shaped, prosthetic devices that are utilized in the cojpensatory treatment of specific clinical structural biomechanical abnormalities of the human foot.

U.S. Pat. No. 4,263,902, issued Apr. 28, 1981 to Dieterich teaches an orthopedic sandal for correction of hammer-toes and X-toe comprising a dual lever arm arrangement pivotable on a horizontal axis transverse to the sole. Additionally, a pressure element for pressing the toes downward in on one arm and the other arm is fastened to the rearward portion of the foot so that as the foot is lifted, the pressure element is pressed downwardly on the hammer-toes.

None of the art as identified above, either individually or in combination, describes an orthopedic shoe appliance nor a method, which specifically provides for improved stability of the foot structure during ambulation, in the manner provided for in the present invention. The present invention provides an orthopedic shoe appliance specifically adapted to provide improved stability of the foot structure, and a method of providing for improved stability of the foot structure, during ambulation. Many individuals suffer from a functional limitation of big toe (hallux) motion with ensuing joint pathology and pain. Additionally, many people suffer from abnormal weight distribution on the ball of the foot with lesser metatarsalgia complaints. Overpronation can be attributed to a host of other foot ailments as well as contributing to abnormal mechanics of the ankle, knee, hip and lower back. This problem is common and has been a topic of concern by shoe manufacturers and podiatrists attempting to achieve foot comfort. The present invention will improve foot function with improved biomechanical noticed immediately as increased foot comfort in the user.

SUMMARY OF THE INVENTION

The goal of the present invention is to provide an orthopedic shoe appliance and a method, which specifically provide for improved stability of the foot structure during ambulation, but do not have the drawbacks and limitations of the devices of the prior art. The orthopedic shoe appliance has a pad suitable for insertion into a shoe, or alternatively, the mid-sole or exterior sole of a shoe. This pad or inner sole can be of any suitable material commonly employed for such purposes, such as flexible material, leather, a resilient foam-like material, cork, thermoplastic, or various combinations of materials. This pad is provided with a wedge which is located on the pad in the area where the big toe would rest on the pad. The wedge provides a means to elevate the big toe up from the top planar surface of the pad and thus up from the floor.

The method includes providing an orthopedic shoe appliance having a pad the pad being provided with a wedge, said wedge being located on the pad in the area where the big toe would rest on the pad. The wedge provides a means to elevate the big toe up from the top planar surface of the pad and thus up from the floor during ambulation. The wedge provides an angle y, said angle y being preferably in the range of from 20 to 30 xdegrees for normal ambulation.

An object of the present invention is to provide an orthopedic shoe appliance which is to be applied to the human foot.

Another object of the present invention is to provide an orthopedic shoe appliance which is to be disposed in footwear and is to be worn for the improved stability of the foot structure during ambulation.

Another object of the present invention is to provide an orthopedic shoe appliance which is easy to manufacture, of relatively low cost to the consumer, and is of sturdy construction to allow for long term use.

Another object of the present invention is to provide a method of providing improved stability of the foot structure during ambulation.

These and other objects are achieved by providing an orthopedic shoe appliance and a method, which specifically provide for improved stability of the foot structure during ambulation.

Further objects and advantages of the present invention will become apparent from the following description reference being had to the accompanying drawings wherein a preferred form of the embodiment of the present invention is clearly shown.

DESCRIPTION OF THE PREFERRED EMBODIMENT

Figure 1:
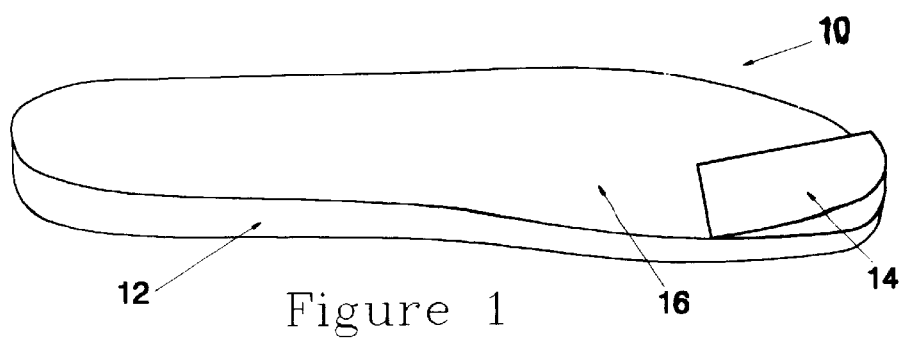
FIG. 1 is a perspective view of the orthopedic shoe apparatus of the present invention showing the pad and the wedge.

Referring now to the drawings, and more particularly to FIG. 1, which is a perspective view of the orthopedic shoe appliance 10 of the present invention, there is shown an orthopedic shoe appliance 10 having a pad 12, said orthopedic shoe appliance being inserted into a shoe, being a mid-sole of a shoe, or being an exterior sole of a shoe. The pad 12 is of any suitable material commonly employed for such purposes, such as flexible material, leather, resilient foam-like material, cork, thermoplastic, or various combinations of materials. This pad 12 is provided with a wedge 14.

The wedge 14 is located on the pad 12 in the area where the big toe would rest on the pad 12. The wedge 14 provides a means to elevate the big toe up from the top planar surface 16 of the pad 12 and thus up from the floor. The overall length and the overall width of the wedge 14 can vary dependant upon the individual big toe to be elevated. The wedge 14 will function to stabilize the first metatarsal against ground reactive forces and limit the displacement of the first metatarsal upward. Thus, the first metatarsal will plantarflex more easily through the late midstance and propulsive phases of gait. By placing the plantar aponeurosis on stretch there will result a retrograde effect at stabilizing the joints more proximally referred to as the midtarsal joint and the subtalar joint with improved joint congruity and alignment of the foot in relationship to the leg during ambulation. When the first metatarsalphalangeal joint is able to dorsiflex 20–30 degrees, normal plantarflexion of the first metatarsal is possible and the normal mechanics of the gait cycle are not disrupted during ambulation. The wedge 14 provides for such 20–30 degree dorsiflexion of the first metatarsalphalangeal joint of the foot.

The relation between the pad 12 and the wedge 14 is defined by an angle y. The angle y is preferably in the range of from 20 to 30 degrees for normal ambulation. The angle y can be either increased or decreased depending upon the amount of correction desired and the heel height of the shoe.

Incorporation of the orthopedic shoe appliance of the present invention into a shoe may require the modification of the shoe toebox to accommodate the elevated big toe and thus to minimize pressure on the top of the big toe.

Figure 2:
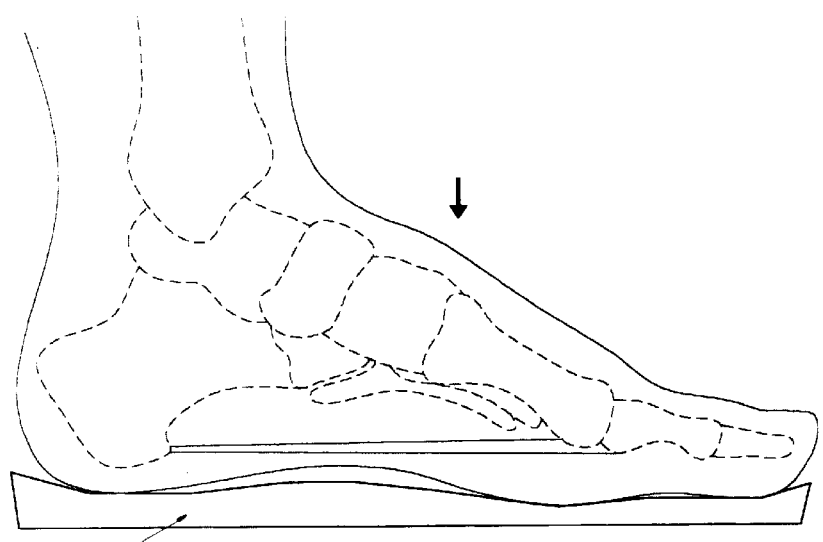
FIG. 2 is a side view of the bone structure of the foot without the orthopedic shoe apparatus of the present invention elevating the big toe.
Figure 3:
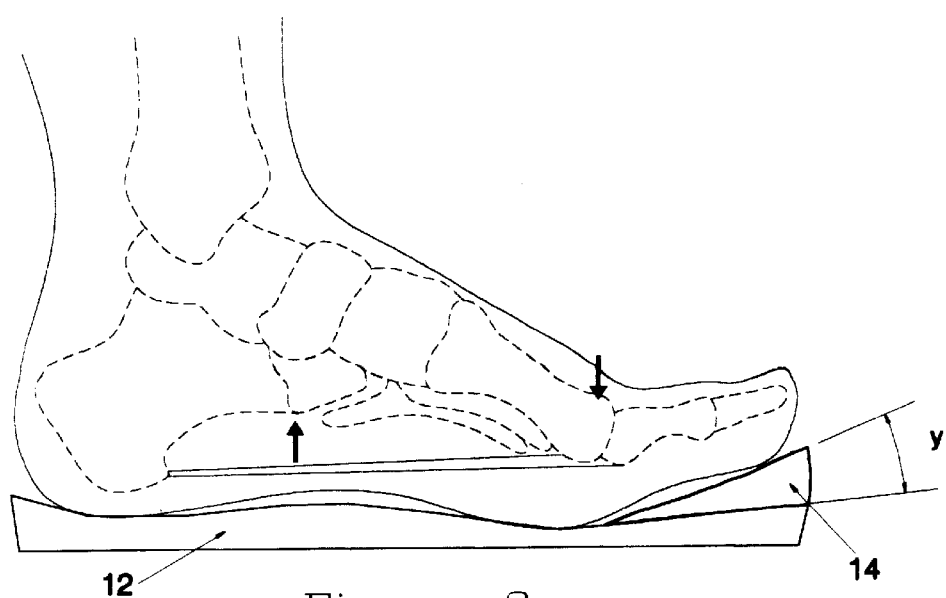
FIG. 3 is a side view of the bone structure of the foot illustrating the orthopedic shoe apparatus of the present invention elevating the big toe.

As shown in FIGS. 2 and 3, a method is provided for improving stability of the foot structure during ambulation. The method includes providing an orthopedic shoe appliance 10 having a pad 12, said pad 12 being inserted into a shoe, said pad 12 being a mid-sole of a shoe, or said pad 12 being an exterior sole of a shoe. Said pad 12 being provided with a wedge 14, said wedge 14 being located on the pad 12 in the area where the big toe would rest on the pad 12. Said wedge 14 providing a means to elevate the big toe up from the top planar surface 16 of the pad 12 and thus up from the floor during ambulation. Said wedge 14 providing an angle y, said angle y being preferably in the range of from 20 to 30 degrees for normal ambulation. Said angle y being either increased or decreased depending upon the amount of correction desired and the heel height of the shoe.

Elevation of the big toe accomplishes several significant biomechanical sequences which have the effect of providing a supinatory position of the joint. As dorsiflexion of the toes takes place in late midstance and early propulsion, the plantar fascia is placed on stretch. As this occurs, the arch height is increased or the distance between the heel and the ball of the foot is shortened. This results in overall supination of the foot structure. A pronated rearfoot and a supinated forefoot (a flat foot) places the aponeurosis (plantar fascia) under stress. Stress without dorsiflexion of the metatarsalphalangeal joints will result in marked limitation of extension of the metatarsalphalangeal joint. It is to be noted that the first metatarsal (big toe) joint has an independent range of motion from the other four metatarsals. As one elevates around the first ray axis the elevated metatarsal limits the ability of the big toe to rotate around the elevated first metatarsal segment. Elevation of the first metatarsal can occur whenever a person overpronates or bears too much weight through the medial (inside) column of the foot. Overpronation is a common biomechanical error in terminal stance and shoe designers for years have been attempting to control abnormal degrees of this motion.

In normal gait, the first metatarsal hits the surface maximally dorsiflexed. After relaxation of the anterior tibial muscle, the first metatarsal should move towards the weight-bearing surface (plantarflex). This is facilitated by rearfoot supination. This plantarflexion is essential for the first metatarsal phalangeal joint to dorsiflex normally in propulsion. The first metatarsalphalangeal joint (big toe joint) must dorsiflex 34 degrees before plantarflexion of the first metatarsal can take place. By placing the big toe in a dorsiflexed position, the first metatarsal is plantarflexed such that excessive dorsiflexion of the first metatarsal cannot occur with weight bearing reactive forces. The net effect of this is to pronate the longitudinal midtarsal joint axis.

Various changes and departures may be made to the invention and method without departing from the spirit and scope thereof. Accordingly, it is not intended that the invention and method be limited to that specifically described in the specification or as illustrated in the drawings but only as set forth in the claims. From the drawings and above-description, it is apparent that an orthopedic shoe appliance constructed in accordance with the invention and method herein provides desirable features and advantages. While the form of the invention and method herein described constitutes a preferred embodiment of the invention, it is to be understood that the invention and method herein are capable of further modification, and this application is intended to cover any variations, uses, or adaption of the invention and method herein, following in general the principles of the invention and method herein and include such departures from the present disclosure as to come within knowledge or customary practice in the art to which the invention and method herein pertain, and as may be applied to the essential features hereinbefore set forth and falling within the scope of the invention and method herein or the limits of the appended claims.

What is claimed and desired to be secured by United States Letters Patent is:

1. An orthopedic shoe appliance, comprising:

a pad;

said pad being inserted into a shoe;

said pad having a wedge;

said wedge being located on said pad in an area where a big toe of a foot would rest on said pad;

said wedge providing a means to elevate said big toe up from a top planar surface of said pad; and, an angle, said angle providing for 20–30 degrees relationship between said pad and said wedge.

2. The orthopedic shoe appliance of claim 1 wherein said pad further comprises being a mid-sole of said shoe.

3. The orthopedic shoe appliance of claim 1 wherein said pad further comprises being an exterior sole of said shoe.

4. The orthopedic shoe appliance of claim 1 wherein said pad further comprises being of suitable flexible material.

5. The orthopedic shoe appliance of claim 1, wherein said pad further comprises leather.

6. The orthopedic shoe appliance of claim 1 wherein said pad further comprises a resilient foam-like material.

7. The orthopedic shoe appliance of claim 1 wherein said pad further comprises latex cork.

8. The orthopedic shoe appliance of claim 1 wherein said pad further comprises thermo-plastic material.

9. The orthopedic shoe appliance of claim 1, wherein said angle is greater than 30 degrees.

10. The orthopedic shoe appliance of claim 1, wherein said angle is less than 20 degrees.

11. A method of providing for improved stability of the foot structure during ambulation, said method comprising the steps of:

providing an orthopedic shoe appliance having a pad, said pad being inserted into a shoe;

said pad being provided with a wedge;

said wedge being located on said pad in an area where a big toe would rest on said pad;

said wedge providing a means to elevate said big toe up from a top planar surface of said pad during ambulation; and, said wedge providing an angle, said angle being in the range of from 20 to 30 degrees between said pad and said wedge.

12. The method of claim 11 further comprising said angle being greater than 30 degrees.

13. The method of claim 11 further comprising said angle being less than 20 degrees.

14. The method of claim 11 wherein said pad further comprises being a mid-sole of said shoe.

15. The method of claim 14 further comprising said angle being greater than 30 degrees.

16. The method of claim 14 further comprising said angle being less than 20 degrees.

17. The method of claim 11 wherein said pad further comprises being an exterior sole of said shoe.

18. The method of claim 17 further comprising said angle being greater than 30 degrees.

19. The method of claim 17 further comprising said angle being less than 20 degrees.

* * * * *